United States Patent
Droit et al.

(10) Patent No.: US 8,436,512 B2
(45) Date of Patent: May 7, 2013

(54) METHOD OF RAPIDLY INTERROGATING ELASTIC WAVE SENSORS

(75) Inventors: Christophe Droit, Besancon (FR); Jean-Michel Friedt, Besancon (FR); Gilles Martin, Chatillon le Duc (FR); Sylvain Ballandras, Besancon (FR)

(73) Assignees: Senseor, Mougins (FR); Centre National de la Recherche Scientifique, Paris (FR)

( * ) Notice: Subject to any disclaimer, the term of this patent is extended or adjusted under 35 U.S.C. 154(b) by 273 days.

(21) Appl. No.: 13/080,508

(22) Filed: Apr. 5, 2011

(65) Prior Publication Data

US 2011/0241482 A1 Oct. 6, 2011

(30) Foreign Application Priority Data

Apr. 6, 2010 (FR) ...................................... 10 52546

(51) Int. Cl.
*H01L 41/107* (2006.01)
(52) U.S. Cl.
USPC .......................................... 310/318; 310/319
(58) Field of Classification Search .................. 310/318, 310/319
See application file for complete search history.

(56) References Cited

U.S. PATENT DOCUMENTS

| 6,316,861 | B1 | 11/2001 | Ballandras et al. |
| 6,362,737 | B1 | 3/2002 | Rodgers et al. |
| 2002/0135270 | A1 | 9/2002 | Ballandras et al. |
| 2005/0162048 | A1 | 7/2005 | Solal et al. |
| 2010/0289380 | A1 | 11/2010 | Ballandras et al. |
| 2010/0313398 | A1 | 12/2010 | Chommeloux et al. |
| 2010/0332157 | A1 | 12/2010 | Friedt |
| 2011/0012477 | A1 | 1/2011 | Chommeloux et al. |

FOREIGN PATENT DOCUMENTS

| WO | 03/019461 A1 | 3/2003 |
| WO | 2007/136550 A2 | 11/2007 |
| WO | 2008/015129 A1 | 2/2008 |

OTHER PUBLICATIONS

J.M. Friedt, et al., "A Wireless Interrogation System Exploiting Narrowband Acoustic Resonator for Remote Physical Quantity Measurement", Review of Scientific Instruments, Jan. 11, 2010, pp. 14701-1-14701-9, vol. 81, No. 1, AIP, Melville, NY, USA, XP012134609.

*Primary Examiner* — Thomas Dougherty
(74) *Attorney, Agent, or Firm* — Baker Hostetler LLP

(57) ABSTRACT

A method of remotely interrogating a passive sensor, comprising at least one resonator, so as to determine the resonant frequency of said resonator, having a resonant frequency response defined by the design of said resonator, includes: a preliminary frequency-scan step for interrogating said resonator over a frequency range allowing for the rapid determination of a first resonant frequency ($fr_0$) of said resonator by detecting the amplitude of the response signal of said resonator; a first step of a first couple of interrogations of said resonator at a first frequency ($f_{11}$) and a second frequency ($f_{21}$) such that: $f_{11}=fr_0-f_m/2$ and $f_{21}=fr_0+f_m/2$, $f_m$ being smaller than the width at half-maximum of the resonant frequency response defined by the design, allowing a first couple of amplitudes ($Pf_{11}$, $Pf_{21}$) of first and second reception signals to be defined; a second step of determining the amplitude difference ($\Delta(Pf_{11}-Pf_{21})$), said difference being signed; a third step allowing a first resonant frequency ($fr_1$), controlled by said signed amplitude difference, to be defined and having the formula $fr_1=fr_0+K^*[\Delta(Pf_{11}-Pf_{21})-Ca]$, where Ca is a control set-point and K is a constant; and the reiteration of the first, second and third steps comprising the definition of an (i+1)th resonant frequency ($fr_{i+1}$) from an ith resonant frequency ($fr_i$) having the formula: $fr_{i+1}=fr_i+K^*[\Delta(Pf_{1i}-Pf_{2i})-Ca]$, so as to obtain a determined resonant frequency ($fr_{i+1}$) such that the signed amplitude difference ($\Delta(Pf_{1i}-Pf_{2i})$) is equal to the control set-point (Ca).

6 Claims, 3 Drawing Sheets

METHOD OF RAPIDLY INTERROGATING ELASTIC WAVE SENSORS

CROSS-REFERENCE TO RELATED APPLICATION

This application claims priority to foreign French patent application No. FR 1052546, filed on Apr. 6, 2010, the disclosure of which is incorporated by reference in its entirety.

FIELD OF THE INVENTION

The field of the invention is that of devices for interrogating passive sensors and notably surface acoustic wave sensors.

These sensors are known to be used, for example, as temperature or pressure sensors and generally comprise at least one resonator comprising a microstructure deposited on the surface of a piezoelectric substrate. For example, a sensor may typically comprise two comb transducers having interdigitated electrodes placed between reflective gratings. The reflective gratings behave like mirrors and there are therefore resonant frequencies at which the return path in the cavity is equal to an integer number of wavelengths. The resonant modes of these frequencies are excited by the transducer placed between the mirrors.

BACKGROUND

This type of sensor may be remotely interrogated by connecting the input of the transducer to a radio frequency (RF) antenna. When the antenna receives an electromagnetic signal, the latter gives rise to waves on the surface of the substrate which are themselves reconverted into electromagnetic energy in the antenna. Thus, the device, consisting of a set of resonators connected to an antenna, has a response to the resonant frequencies of the resonators that it is possible to measure remotely. It is thus possible to produce remotely interrogable sensors. This possibility is a major advantage of surface acoustic waves and may be used notably in the context of pneumatic pressure sensors. This is because it is advantageous in this type of application to be able to place the sensor in the pneumatics whereas the interrogation electronics are stowed onboard the vehicle.

According to the prior art, remote interrogation systems use interrogation signals in the form of pulses (typically with periods of about 25 µs) which are transmitted via an emitting antenna in the direction of a receiving antenna connected to the surface-wave sensor (referred to below, in the description, as a SAW sensor).

A preferred frequency band for this type of system is the ISM (industrial, scientific and medical) band having a central frequency of 433.9 megahertz, the associated band width being 1.7 megahertz (MHz).

Generally, a remotely interrogable SAW sensor and its interrogation system may comprise, as illustrated in FIG. 1, in the simplified case of a single transducer:
an interrogation system 2; and
at least one resonator 1 comprising;
an antenna 100; and
a comb transducer having interdigitated electrodes 11 and an SAW resonant cavity 13 characterized by its central frequency F and its quality factor Q (corresponding to the ratio between the central frequency and the width of the pass band). The cavity 13 comprises two series of reflectors that are uniformly spaced apart by a distance d. The transducer is connected to the antenna 100.

The interrogator 2 sends a long radio-frequency pulse so as to charge the resonator 1. After the emission has been stopped, the resonator discharges at its resonant eigenfrequency with a time constant $\tau$ equal to $Q/\pi F$. This discharge of the resonator forms the return echo detected by the receiver of the interrogator. Spectral analysis then allows the resonator frequency to be calculated and identified. This analysis may be carried out by algorithms based on Fourier transforms, for example an FFT (fast Fourier transform). This type of spectral-analysis treatment is particularly complex.

A method for remotely interrogating passive SAW-type sensors has been proposed, in patent application WO 2008/015129, based on a frequency-modulation method. More precisely, this patent application discloses a method of measuring the resonant frequency of a resonator comprising the following steps:
emission, in succession, of radio-frequency signals of known carrier and modulation frequency, including the resonant frequency;
reception, via a receiving system, of response waves from the sensor; and
spectral analysis of the response waves from the sensor.

The RF emission is frequency modulated with a modulation $\omega_m$ and an amplitude modulation typically of about a kHz.

The response signal of the sensor is amplitude modulated with a modulation frequency $\omega_m$.

The measurement principle described above is based on the conversion of an (emitted) frequency modulation into an amplitude modulation via the transfer function of the resonator, as illustrated in FIG. 2. An emission modulated at an angular frequency $\omega_m$ (corresponding frequency $f_m$) results in the power detector receiving a signal modulated at the frequency $\omega_m$ but more importantly, in a possible phase inversion of the modulated signal depending on whether it is below or above the resonant frequency.

The sinusoid, injected in the signal, at the frequency $\omega_m$, representing the modulating signal, is either directly converted into an amplitude modulation by the transfer function of the resonator (positive slope beneath the resonant frequency, amplitude modulation in phase with the frequency modulation), or inverted (negative slope above the resonant frequency, amplitude modulation in antiphase with the frequency modulation). The intermediate point corresponds to a null contribution to the received signal at the modulation frequency $f_m$.

Around this frequency position, the amplitude of the component of the signal at the frequency $f_m$ varies linearly.

The applicant observed that when implementing an algorithm providing the function described above, namely transformation of the contribution to the modulation frequency into a signed datum around the null contribution to the modulation frequency $f_m$, and when detecting the amplitude, although a sinusoid is emitted to generate the frequency modulation, it is possible to use only two components of the received signal, respectively at the maximum and minimum modulation frequencies, this observation allowing interrogation times to be very substantially reduced.

SUMMARY OF THE INVENTION

The subject of the present invention is a method of interrogation that uses the phase rotation present in the response of the received signal of the prior art mentioned above to extract from the sensor response around this null point a datum called a signed datum, i.e. a datum that is positive or negative, favourable to the implementation of a control loop for defining with precision the resonant frequency of the resonator, and this in a much shorter interrogation time than in the prior art mentioned.

More precisely, the subject of the present invention is a method of remotely interrogating a passive sensor, comprising at least one resonator, so as to determine the resonant frequency of said resonator, having a resonant frequency response defined by the design of said resonator, characterized in that the method comprises the following steps:

a preliminary frequency-scan step for interrogating said resonator over a frequency range determined by the design of said resonator, allowing for the rapid determination of a resonant frequency response centred on a preliminary resonant frequency $fr_0$ located between a lower preliminary frequency $fr_{pi}$ and a higher preliminary frequency $fr_{ps}$ defined at the half-maximum of said resonant frequency response of said resonator by detecting the amplitude of the response signal of said resonator;

a first step of a first couple of interrogations of said resonator at a first frequency $f_{11}$ and a second frequency $f_{21}$ such that: $f_{11}=fr_0-f_m/2$ and $f_{21}=fr_0+f_m/2$, with: $f_m < fr_{ps}-fr_{pi}$ and allowing a first couple of amplitudes $Pf_{11}$ and $Pf_{21}$ of first and second received signals to be defined;

a second step of determining the amplitude difference $\Delta(Pf_{11}-Pf_{21})$ between the first and second signals, said difference having a positive or negative sign;

a third step allowing a first resonant frequency $fr_1$, controlled by said signed amplitude difference, to be defined and having the following formula:

$fr_1=fr_0+K*[\Delta(Pf_{11}-Pf_{21})-Ca]$, where Ca is a control set-point and K is a constant; and the reiteration of the first, second and third steps and the definition of an (i+1)th resonant frequency from an ith frequency having the following formula:

$$fr_{i+1}=fr_i+K*[\Delta(Pf_{1i}-Pf_{2i})-Ca],$$

so as to obtain a determined resonant frequency ($fr_{i+1}$) such that the signed amplitude difference $\Delta(Pf_{1i}-Pf_{2i})$ is equal to the control set-point Ca.

According to one variant of the invention, the preliminary frequency-scan step for interrogating said resonator over a band of frequencies, allowing for the rapid determination of a first resonant frequency $fr_0$ of said resonator, is carried out with frequency steps equal to about a third of the width at half-maximum of the resonant frequency response, defined by the design of said resonator.

According to one variant of the invention, the frequency band is the ISM band.

According to one variant of the invention, the frequency $f_m$ is lower than a few tens of kilohertz (kHz).

According to one variant of the invention, the control set-point is zero.

According to one variant of the invention, the constant K is equal to 1.

BRIEF DESCRIPTION OF THE DRAWINGS

The invention will be better understood and other advantages will become clear on reading the following description given by way of non-limiting example and by virtue of the appended figures in which.

DETAILED DESCRIPTION

According to the present invention, the interrogation method thus comprises a preliminary frequency-scan step for interrogating said resonator over a frequency range known from the very design of the resonator concerned, allowing for the rapid determination of a first resonant frequency $fr_0$ of said resonator by detecting the amplitude of the response signal of said resonator. Typically it will be advantageous for many applications to use the ISM band mentioned above (or another ISM band compatible with the use of radio-frequency resonators, in particular elastic-wave resonators).

Figure 1:
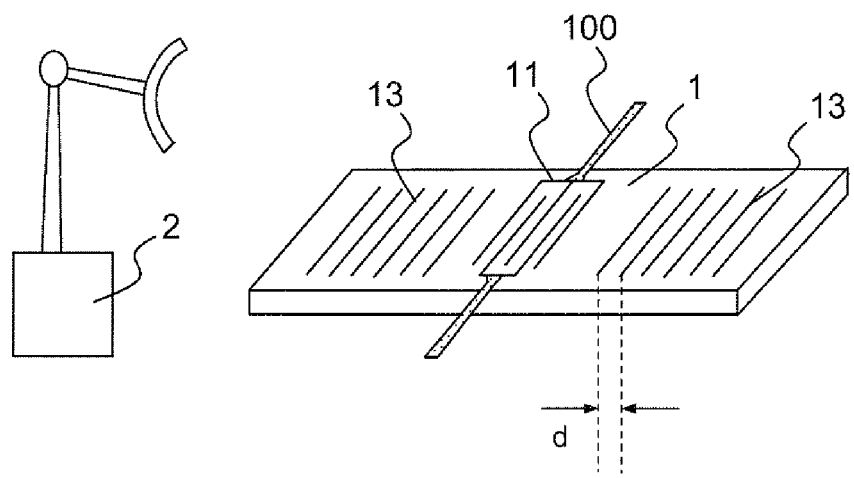
FIG. 1 illustrates the principle of interrogation of a SAW sensor according to the prior art.
Figure 3:
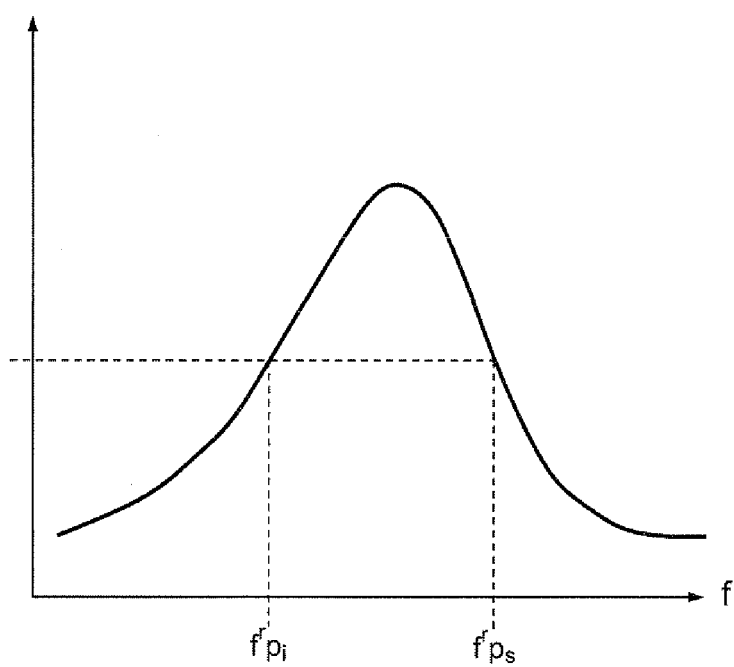
FIG. 3 illustrates the preliminary frequency-scan step allowing the frequencies $f_{rpi}$ and $f_{rps}$ to be determined.
Figure 2:
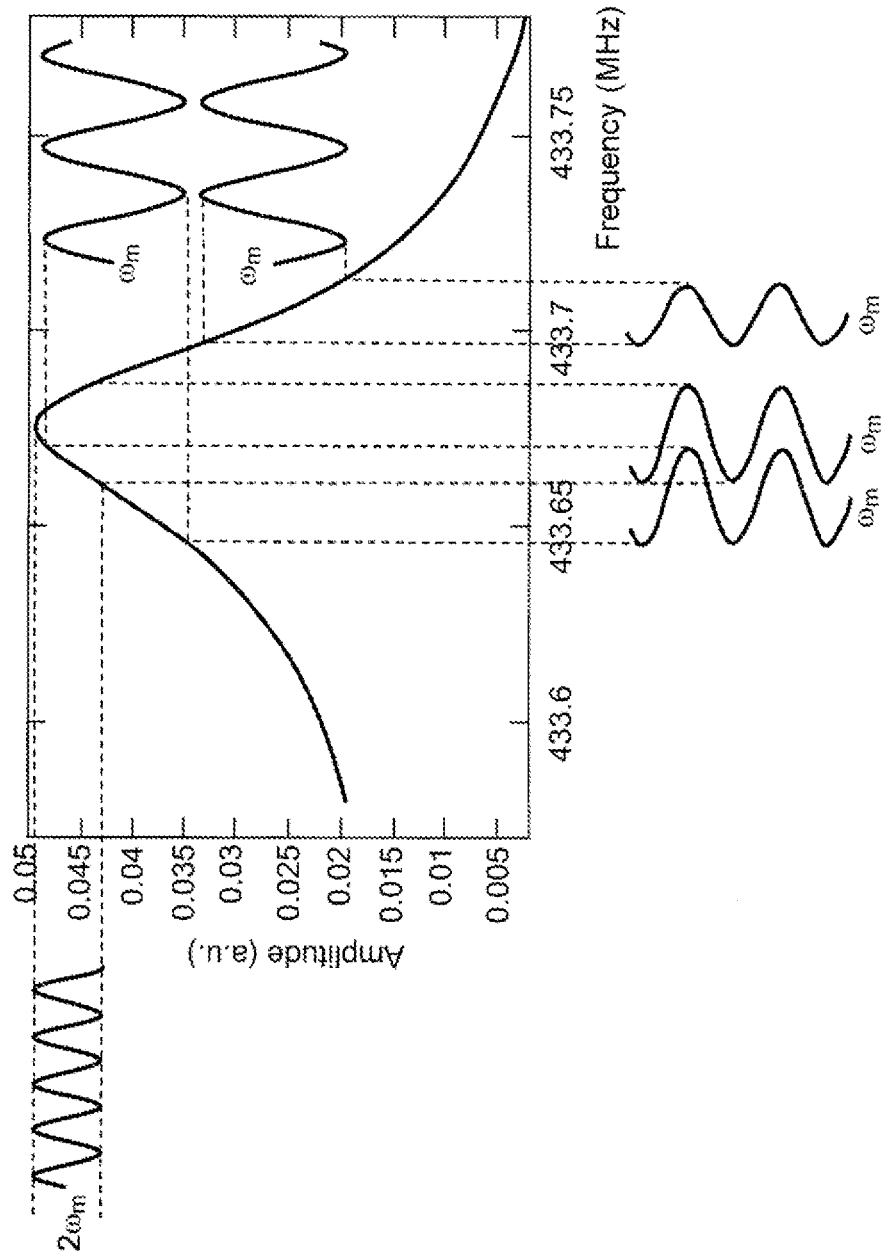
FIG. 2 illustrates the conversion of an (emitted) frequency modulation into an amplitude modulation via the transfer function in an interrogation method according to the prior art.

FIG. 3 illustrates a frequency response curve on which it is possible to define the preliminary resonant frequency and the two frequencies $fr_{pi}$ and $fr_{ps}$ allowing the frequency $f_m$, which is chosen to be lower than the difference $fr_{ps}-fr_{ps}$, to be determined.

It should be noted that a compromise between the returned power and the measurement precision affects the choice of the interval between the interrogation frequencies. This is because, the further these frequencies are from the resonant frequency, the less power is received on return, but the greater the measurement precision nonetheless.

The applicant has observed that the frequency $f_m$ does not seem to affect the measurement resolution when it lies between 1 kHz and 50 kHz. However, choosing too high a frequency $f_m$ reduces the range of the measurement, the resonator not being very effective far from its resonance. Typically the ISM band, centred on 433.9 MHz, and a frequency $f_m$ of about 10 kHz will possibly be chosen.

The interrogation method of the invention is then carried out iteratively.

Figure 4:
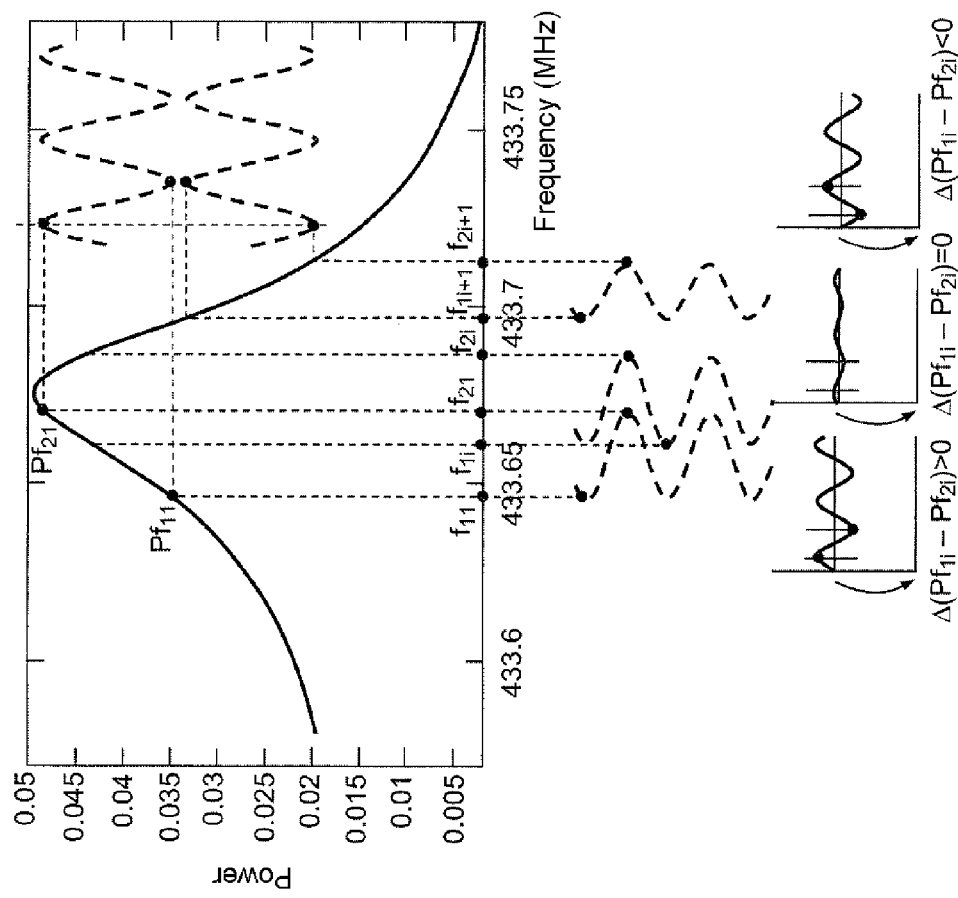
FIG. 4 illustrates the interrogation couples and the determination of the signed power difference used in the present invention.

In a first step, the interrogation is initiated at a first frequency $f_{11}$ and at a second frequency $f_{21}$ such that: $f_{11}=fr_0-f_m/2$ and $f_{21}=fr_0+f_m/2$, allowing a first couple of amplitudes $Pf_{11}$, $Pf_{21}$ of first and second reception signals to be defined, as illustrated in FIG. 4.

In a second step, the amplitude difference $\Delta(Pf_{11}-Pf_{21})$ is determined, said difference having a sign.

In a third step, a first resonant frequency $fr_1$ controlled by said signed amplitude difference is defined and has the following formula:

$fr_1=fr_0+K*[\Delta(Pf_{11}-Pf_{21})-Ca]$, where Ca is a control set-point and K is a constant.

The first, second and third steps are then reiterated, comprising the definition of an i+1th resonant frequency having the following formula:

$$fr_{i+1}=fr_i+K*[\Delta(Pf_{1i}-Pf_{2i})-Ca],$$

so as to obtain a determined resonant frequency $fr_{i+1}$ such that the signed amplitude difference $\Delta(Pf_{1i}-Pf_{2i})$ is equal to the control set-point Ca.

For example, Ca may be chosen to equal 0.

With Ca equal to 0, the iteration process is stopped when $\Delta(Pf_{1i}-Pf_{2i})=0$.

Thus, and according to the invention, the signal received for the first frequency $f_{11}=fr_0-f_m/2$ contains total power (or amplitude) information corresponding to an average value and a low-frequency modulation contribution that may be considered as "virtual". The signal received at the second frequency $f_{21}=fr_0+f_m/2$ contains total power (or amplitude) information corresponding to an average value and a high-frequency modulation contribution that may be considered to be "virtual".

The contribution of the average value is then eliminated during calculation of the difference in the powers received at the frequencies $f_{11}$ and $f_{21}$ so as to extract only the contribution of the modulation signal. The difference in the powers received at each frequency yields a datum the sign of which will depend on the position relative to the frequency $f_{r0}$. Thus according to the invention, it is proposed to carry out an iterative function allowing the residual mentioned above to be cancelled out. This step may be carried out using a bisection method, a Newton-Raphson method or any other method allowing a more rapid convergence of the iterative process.

Thus any method capable of determining the root of a function is particularly suitable in this case. The bisection method is an approach consisting in reducing the search interval in which a root of the function considered is looked for by comparing the signs of this function after estimation. The data points considered are always chosen such that they are of opposite sign. The interval is divided by two then a new interval is identified for which the new data points are of opposite sign. This process continues until a convergence criterion is met. The Newton-Raphson method is based on the use of the first order Taylor series near the root to be identified. For each new set of data points, the first derivative of the curve is calculated for the data point furthest from the root and the first derivative is used to derive an estimation of the root. The more regular and monotonic the curve is near the desired point the smaller the number of iterations required for the process to converge. These examples are given by way of illustration and may advantageously be replaced by more efficient (Müller, etc) methods. In this context, a useful reference is: A. Angot, Compléments de mathématiques, Masson Ed., 6th Edition, 1982, and internationally Abramowitz and Stegun. Handbook of Mathematical Functions, on-line at http://people.math.sfu.ca/~cbm/aands/

Thus the frequency $fr_0$ is controlled to coincide with the resonant frequency of the sensor interrogated. This control is similar to a phase-locked loop the target-frequency detection stability and precision characteristics of which are better than the elements of this measurement in an open loop.

The invention claimed is:

1. A method of remotely interrogating a passive sensor, comprising at least one resonator, so as to determine the resonant frequency of said resonator, having a resonant frequency response defined by the design of said resonator, the method comprising:
   a preliminary frequency-scan step for interrogating said resonator over a frequency range determined by the design of said resonator, allowing for the rapid determination of a resonant frequency response centred on a preliminary resonant frequency ($fr_0$) located between a lower preliminary frequency ($fr_{pi}$) and a higher preliminary frequency ($fr_{ps}$) defined at the half-maximum of said resonant frequency response of said resonator by detecting the amplitude of the response signal of said resonator;
   a first step of a first couple of interrogations of said resonator at a first frequency ($f_{11}$) and a second frequency ($f_{21}$) such that $f_{11}=fr_0-f_m/2$ and $f_{21}=fr_0+f_m/2$, with $f_m<f_{ps}-fr_{pi}$, allowing a first couple of amplitudes ($Pf_{11}$, $Pf_{21}$) of first and second reception signals to be defined;
   a second step of determining the amplitude difference ($\Delta(Pf_{11}-Pf_{21})$) between the first and second signals, said difference being positively or negatively signed;
   a third step allowing a first resonant frequency ($fr_1$), controlled by said signed amplitude difference, to be defined and having the formula $fr_1=fr_0+K*[\Delta(Pf_{11}-Pf_{21})-Ca]$, where Ca is a control set-point and K is a constant; and
   wherein the first, second and third steps are reiterated and an (i+1)th resonant frequency ($fr_{i+1}$) from an ith resonant frequency ($fr_i$) is defined having the formula $fr_{i+1}=fr_i+K*[\Delta(Pf_{1i}-Pf_{2i})-Ca]$, so as to obtain a determined resonant frequency ($fr_{i+1}$) such that the signed amplitude difference ($\Delta(Pf_{1i}-Pf_{2i})$) is equal to the control set-point (Ca).

2. A method of remotely interrogating a passive sensor according to claim 1, in which the preliminary frequency-scan step for interrogating said resonator over a band of frequencies, allowing for the rapid determination of a first resonant frequency ($fr_0$) of said resonator, is carried out with frequency steps equal to about a third of the width at half-maximum of the resonant frequency response.

3. A method of remotely interrogating a passive sensor according to claim 1, in which the band of frequencies is an ISM band, and more particularly that centred on 433.9 MHz.

4. A method of remotely interrogating a passive sensor according to claim 1, in which the frequency $f_m$ is lower than a few tens of kilohertz.

5. A method for remotely interrogating a passive sensor according to claim 1, in which the control set-point is zero.

6. A method of remotely interrogating a passive sensor according to claim 1, in which the constant K is equal to 1.

* * * * *